United States Patent [19]
Mills

[11] Patent Number: 5,814,721
[45] Date of Patent: Sep. 29, 1998

[54] FLUID BOILING POINT ANALYZER

[75] Inventor: Lionel William Mills, Kinghorn, Scotland

[73] Assignee: Alba Tools Limited, Glenrothes, Scotland

[21] Appl. No.: 737,566

[22] PCT Filed: May 10, 1995

[86] PCT No.: PCT/GB95/01060

§ 371 Date: Nov. 11, 1996

§ 102(e) Date: Nov. 11, 1996

[87] PCT Pub. No.: WO95/30899

PCT Pub. Date: Nov. 16, 1995

[30]     Foreign Application Priority Data

May 10, 1994  [GB]  United Kingdom ................... 9409296

[51] Int. Cl.$^6$ ........................... G01N 25/08; G01N 33/28
[52] U.S. Cl. .......................... 73/53.01; 73/61.76; 374/16; 374/25; 374/164
[58] Field of Search ............................... 73/61.76, 53.01; 374/16, 21, 25, 27, 54, 164, 170

[56]            References Cited

U.S. PATENT DOCUMENTS

| | | |
|---|---|---|
| 2,599,276 | 6/1952 | Norman . |
| 3,084,535 | 4/1963 | Markey . |
| 4,109,527 | 8/1978 | Goode, Jr. . |
| 4,408,902 | 10/1983 | Peuker ...................................... 374/27 |
| 4,484,822 | 11/1984 | Hancock . |
| 4,484,823 | 11/1984 | Peuker . |
| 4,562,554 | 12/1985 | Stixrud et al. . |
| 4,648,055 | 3/1987 | Ishizaka et al. . |
| 4,718,776 | 1/1988 | Gilland et al. . |
| 4,735,512 | 4/1988 | Suzuki . |
| 4,958,937 | 9/1990 | Lohberg et al. ........................... 374/16 |
| 5,380,091 | 1/1995 | Buchanan .................................. 374/16 |

FOREIGN PATENT DOCUMENTS

| | | |
|---|---|---|
| 0056424 | 7/1982 | European Pat. Off. . |
| 0074415 | 3/1983 | European Pat. Off. ................. 374/16 |
| 3910242 | 10/1990 | Germany . |
| 01-280244 | 11/1989 | Japan . |
| 2139763 | 11/1984 | United Kingdom . |
| 2287321 | 9/1995 | United Kingdom ...................... 374/16 |
| 0004249 | 7/1987 | WIPO ...................................... 374/27 |
| 0012311 | 10/1990 | WIPO ...................................... 374/16 |
| 0024646 | 9/1995 | WIPO ...................................... 374/16 |

OTHER PUBLICATIONS

*Dosatherm 300* —1989 —Promotional Literature and Technical Information Sheet.
IBM Technical Disclosure Bulletin —vol. 13, No. 8, Jan. 1971, p. 2402 "Float type boiling point sensor" (Aakaluctal).

*Primary Examiner*—Hezron E. Williams
*Assistant Examiner*—Daniel S. Larkin
*Attorney, Agent, or Firm*—Young & Basile, P.C.

[57]            ABSTRACT

The present invention provides an apparatus for use in indicating the boiling point of fluids across a wide temperature range which comprises a meter of the portable hand-held type including a probe for insertion vertically into a fluid for testing, with heating means in the probe for heating of the fluid, and monitoring means for monitoring the temperature rise of heated fluid for indicating the boiling point temperature of the fluid. The probe portion has an inner chamber, in which are located the heating means and temperature monitoring means, and which is provided with thermal insulation means for restricting heat loss from the inner chamber during heating up of the fluid in the inner chamber up to its boiling point. The inner chamber is provided with port means formed and arranged for allowing entry of fluid into the inner chamber upon immersion of the probe portion into the fluid for semi-encapsulation of fluid in the inner chamber and substantially restricting loss of heated fluid therefrom to the exterior during heating up of the fluid in the inner chamber up to its boiling point, while allowing loss of boiling fluid to the exterior thereby substantially increasing heat loss from the inner chamber once the fluid has been heated to its boiling point.

12 Claims, 4 Drawing Sheets

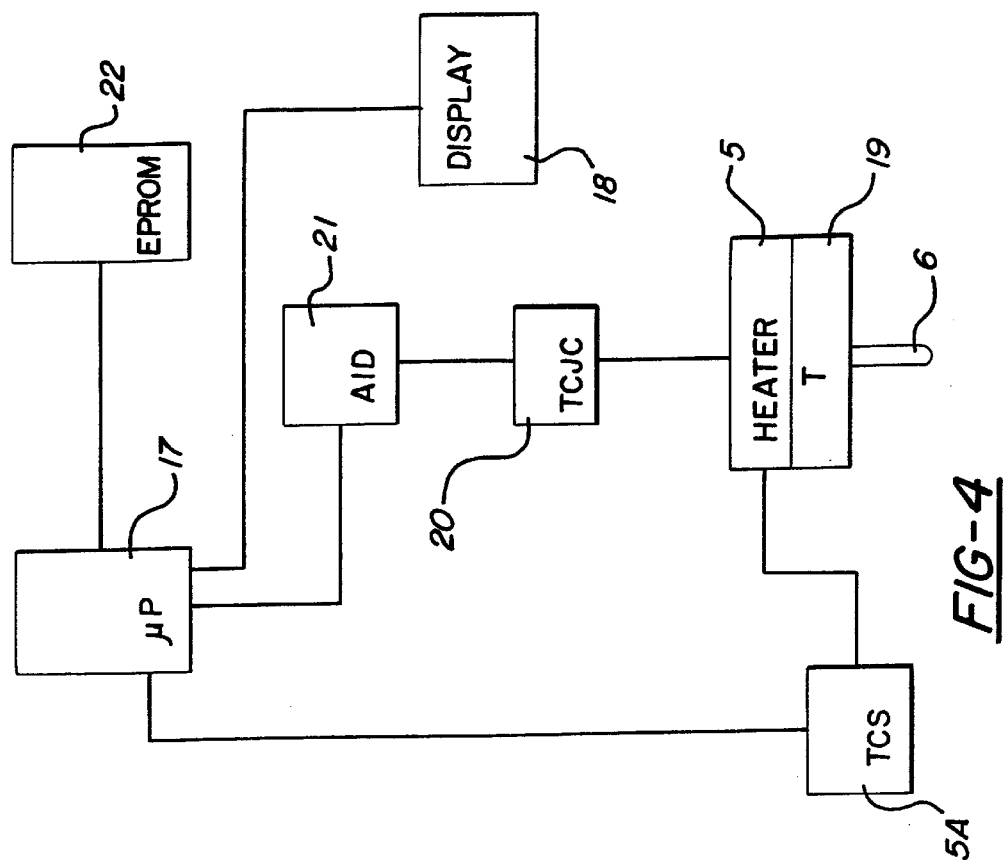
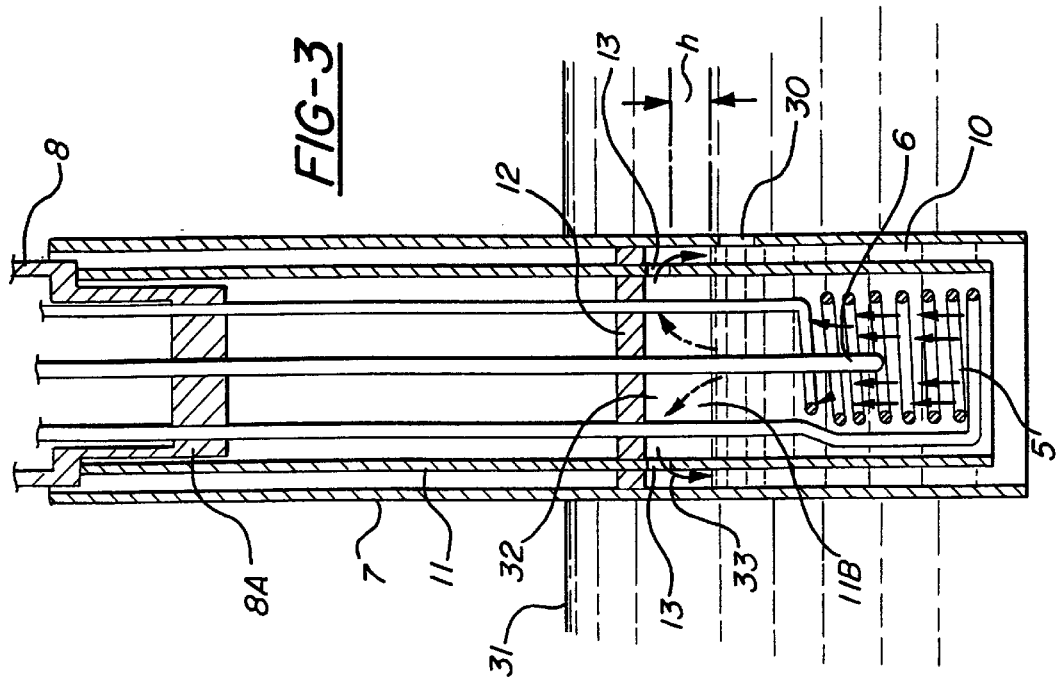

FLUID BOILING POINT ANALYZER

BACKGROUND OF THE INVENTION

The present invention relates to a fluid analyzer suitable for use in indicating the boiling point of fluids especially hygroscopic fluids such as hydraulic fluids, for example automotive brake and clutch fluid thereby to monitor the fluid for possible contamination thereof with water etc.

Brake fluid as used in the hydraulic braking systems of motor-cars and vans is hygroscopic i.e. is capable of absorbing moisture, and this can have an adverse effect on braking performance especially in the long term. In particular, the absorption of moisture in the brake fluid causes a lowering of the boiling point of the fluid and very possibly to such a degree that a temperature increase in the braking system due for example to heavy braking or some fault condition can result in the brake fluid boiling and as will be appreciated this has a very deleterious effect on braking. Therefore, it is beneficial to be aware of a serious lowering of the boiling point of brake fluid so that steps can be taken to change the faulty fluid.

Several devices have been previously proposed for this purpose but have suffered from various disadvantages such as being cumbersome and only suitable for laboratory use; providing unstable cyclically fluctuating outputs which make it difficult to obtain reliable accurate results; not being particularly accurate; and/or forming noxious vapours due to the evaporation of hydraulic fluid; and needing to be immersed to a precise depth.

SUMMARY OF THE INVENTION

It is an object of the present invention to avoid or minimize one or more of these disadvantages.

The present inventor has recognized that where it is desired to measure the boiling points of fluids with widely differing boiling point values e.g. anywhere between 120° C. and 260° C., problems arise due to the widely differing heat loss rates. Thus, at higher temperatures there is a relatively large heat loss rate requiring a relatively high heat input rate in order to sustain boiling of the fluid. On the other hand, at lower temperatures there is a substantially lower heat loss rate so that if a high heat input rate is used there will be excessive uncontrolled vaporization and toxic, or at least unpleasant, smoke generation. Thus the present inventor has found that in order to provide an apparatus suitable for monitoring a relatively wide temperature range as is often the case with motor vehicle applications involving a wide range of hydraulic brake and clutch fluids and the like, it is necessary to provide an apparatus which can automatically adapt to these widely differing thermal requirements.

The present invention pro rides an apparatus for use in indicating the boiling point of fluids across a wide temperature range which apparatus comprises a meter of the portable hand held type including a probe portion for insertion substantially vertically into fluid in a fluid reservoir for fluid testing, heating means being provided in the probe portion for heating of said fluid, said meter including monitoring mean for monitoring the temperature rise of fluid heated by said heating means for use in indicating the boiling point temperature of the fluid, said probe portion having an inner chamber, in which are located said heating means and said temperature monitoring means, said inner chamber being provided with thermal insulation means for restricting heat loss from said inner chamber, in use of the apparatus, during heating up of said fluid in the inner chamber up to its boiling point, said inner chamber being provided with port means formed and arranged for allowing entry of fluid into said inner chamber upon immersion of the probe portion into said fluid for semi-encapsulation of fluid in the inner chamber and substantially restricting loss of heated fluid therefrom to the exterior during said heating up of said fluid in the inner chamber up to its boiling point, whilst allowing loss of boiling fluid to the exterior thereby substantially increasing heat loss from aid inner chamber once said fluid has been heated to its boiling point.

Thus with an apparatus of the present invention it is possible to obtain quickly, reliable and accurate boiling point temperature measurements from various fluids with a wide range of boiling points, and especially vehicle brake fluids within the range 120° to 260° C. without having to immerse the probe to an exact depth.

It will be appreciated that in practice the boiling point of brake fluid which has become contaminated with water increases as boiling continues. This is because the water is gradually distilled of and this contrasts very strongly with the boiling point of pure materials like water. The measurement of brake fluid boiling point conventionally uses the ERBP (equilibrium reflux boiling point) test. This specifies a precise apparatus with a fixed quantity of fluid and various other precise details. As the test proceeds, the temperature initially rises steadily, then rises more slowly as boiling commences, reaches a peak, and then falls before eventually settling down at the ERBP. The reason for this odd behavior is that initially, the water is mixed throughout the fluid but eventually, enough is driven off as steam to condense on the walls of the flask. At this point the curve has risen and come to a maximum. Further water deposited on the flask causes runs and drips of condensed water back into the boiling fluid. This immediately reboils off but in doing so, reduces the temperature. Eventually, equilibrium is reached but at this point, a significant amount of water has been boiled off in the form of drops on the flask walls and the quantity of this is dependent on many things which are not specified like the rate of cooling water flow, the ambient temperature in the room, drafts, and how the flask was washed previously etc. This results in different laboratories obtaining different measurements for the same fluid, i.e. the reference ERBP test itself is not very good. Thus, for example, with a DOT3 brake fluid containing 2% v/v of moisture the boiling point is reduced to 170° C. from that of uncontaminated brake fluid which is 270° C. Boiling can reduce the moisture content to 1% v/v though leading to a rise in the boiling point to over 200° C. We test our reference fluid in our ERBP apparatus but find we need to correct both for the fact that our meter detects the commencement of boiling and not the ERBP, as well as the fact that the customer's laboratory may have different test conditions to us. Thus, the meter of the present invention actually detects more closely what matters to a motor vehicle user, i.e. the commencement of boiling of its brake fluid and not the ERBP which is actually higher because of the water that has boiled out of the fluid onto the flask walls. Nevertheless, it is possible, if desired, to apply a correction of a few degrees to the boiling temperature measurement obtained with a meter of the present invention to relate it more closely to an ERBP measurement and thus to the temperature range limits normally used for specifying the acceptability of brake fluids.

A suitable correction can readily be determined by simple experiment: a sample of brake fluid has its "boiling point" measured using conventional ERBP apparatus. A number (e.g. three) measurements are then made using a meter of the present invention and the average compared with the ERBP reading. In a typical example the average may be 145° C.

whilst the ERBP measurement is 150° C. The meter is then 'calibrated' by applying an offset of +5° C. to obtain an ERBP "compatible" measurement. Conveniently, the offset is applied automatically by programming a microprocessor provided in the meter, using technique s known in the art.

The inner chamber may be thermally insulated in any convenient manner including, for example, the use of wall means of a thermally insulating material. Another convenient form of insulation means comprises the provision of a generally annular outer chamber for semi-encapsulating fluid which upon warning by some heat loss from the inner chamber, tends to restrict further heat loss from the inner chamber to the main body of fluid on the exterior of the probe portion.

Various forms of fluid port means may be provided for restricting entry and/or exit of fluid into and from the inner chamber, respectively. Thus, for example, there may be used valve means, especially one-way valve means, of various forms including ball valves and flap valves and the like. These may moreover be formed and arranged for sensing fluid boiling directly e.g. by being formed and arranged so as to be operable in response to pressure fluctuations associated with boiling. Alternatively, there may be provided port opening means, e.g. electromechanical ones, provided with control means including sensor means for sensing fluid boiling by any convenient means including pressure fluctuation sensing means, acoustic sensor means, etc.

In the case of those embodiments where the insulation means is in the form of an outer chamber, then a particularly convenient form of port means for selectively restricting fluid loss from the inner chamber comprises a "weir" means i.e. a passage means extending upwardly from a fluid fill level in the inner chamber substantially defined by an opening in the outer wall or casing of the outer chamber, over a barrier at a predetermined elevation above said opening in the outer wall or casing, into the outer chamber (see also detailed description hereinbelow). It is important that the elevation should be not so great as to prevent escape of boiling fluid along said passage over said barrier. Suitable elevations can be readily determined by simple trial and error with monitoring of the form of the temperature measured by said temperature monitoring means. Where the elevation is too small then there is a risk of increased heat loss before boiling occurs resulting in a shallower temperature gradient and increase in time to attain boiling temperature Where the elevation is too great then fluid loss is substantially delayed or may not occur at all leading to over-heating or super-heating and/or violent pressure fluctuations in the inner chamber leading to uncontrolled fluid exchange with cold fluid being drawn in periodically and an irregular temperature profile. In general we have found that a suitable elevation is in the region from 1 to 5 mm, preferably from 2 to 4 mm, e.g. approximately 3 mm.

In a preferred aspect, the present invention provides an apparatus for use in indicating the boiling point of fluids across a wide temperature range which apparatus comprises a meter of the portable hand held type including a probe portion for insertion substantially vertically into fluid in a fluid reservoir for fluid testing, heating means being provided in the probe portion for heating of said fluid, said meter including monitoring means for monitoring the temperature rise of fluid heated by said heating means for use in indicating the boiling point temperature of the fluid, said probe portion having an outer casing, an inner casing within the outer casing and defining an inner chamber within the inner casing, and a generally annular chamber between the inner casing and the outer casing, said heating means being located in the inner chamber together with the temperature monitoring means, said inner chamber being provided with port means formed and arranged for allowing entry of fluid into said inner chamber upon immersion of the probe portion into said fluid for semi-encapsulation of fluid in the inner chamber and substantially restricting loss of heated fluid there from to the exterior during said heating up of said fluid in the inner chamber up to its boiling point, whilst allowing loss of boiling fluid to the exterior thereby substantially increasing heat loss from said inner chamber once said fluid has been heated to its boiling point, said port means including passage means extending upwardly from a fluid fill level in the inner chamber substantially defined by an opening in the outer wall or casing of the outer chamber, over a barrier at a predetermined elevation above said opening in the outer wall, or casing, into the outer chamber.

In a further aspect, the present invention provides an apparatus for use in indicating the boiling point of fluids across a wide temperature range in a particularly convenient, economic and reliable manner, which apparatus comprises a meter of the portable hand held type including a probe portion for insertion substantially vertically into fluid in a fluid reservoir for fluid testing, heating means being provided in the probe portion for heating fluid in which the probe portion is inserted, said meter including monitoring means for monitoring the temperature rise of fluid heated by said heating means for use in indicating the boiling point temperature of the fluid, said probe portion having an outer casing, an inner casing within the outer casing and defining an inner chamber within the inner casing, and a generally annular chamber between the inner casing and the outer casing, said heating means being located in the inner chamber together with the temperature monitoring means, said outer casing having a first fluid port means substantially below the upper end of said inner chamber, and said inner casing having a second fluid port means at a level between the first fluid port means and the upper end of said inner clamber so that in use of the apparatus a portion of fluid can be semi-encapsulated in the inner chamber and be heated rapidly up to its boiling point therein whilst remaining substantially contained therein, and upon vigorous boiling thereof said fluid portion can overflow through said second fluid port means out of said inner chamber thereby increasing the rate of heat loss therefrom.

The present invention also extends to a method of measuring the boiling point of a fluid comprising the steps of providing an apparatus of the present invention; inserting the probe portion thereof into a body of said fluid; activating said heating means; and monitoring the temperature rise of fluid heated by the heating means with said monitoring means of the meter of said apparatus.

Insofar as the apparatus of the present invention can rapidly reach a substantially steady state boiling temperature measurement output this facilitates the processing or interpretation of a moderately fluctuating output such as normally occurs under boiling conditions e.g. by allowing capture of a series of maxima which can be averaged to provide a final boiling point temperature measurement.

A particular problem of previously known designs is that of obtaining a reliable and steady boiling temperature read out from the temperature monitoring means. A common form of temperature curve has a relatively steep rise following by a partial fall and oscillation around the region of the boiling point as a result of more or less violent boiling, pressure fluctuations and hot and cold fluid exchange around the temperature monitor. Thus the timing of the measurement to obtain a reliable indication of boiling temperature becomes a significant problem.

With the present invention though there may be obtained a rapid initial temperature rise which then flattens off more or less smoothly to a plateau providing a more or less steady temperature reading which can then be reliably measured.

Further preferred features and advantages of the present invention will appear from the following detailed description given of two preferred embodiments illustrated with reference to the accompanying drawings wherein:

BRIEF DESCRIPTION OF THE DRAWINGS

FIG. 3 shows the lower part of the probe portion of FIG. 2 on a larger scale;

FIG. 4 is a schematic block circuit diagram of known general form suitable for use in the apparatus of FIG. 1.

DESCRIPTION OF THE PREFERRED EMBODIMENTS

Figure 1:
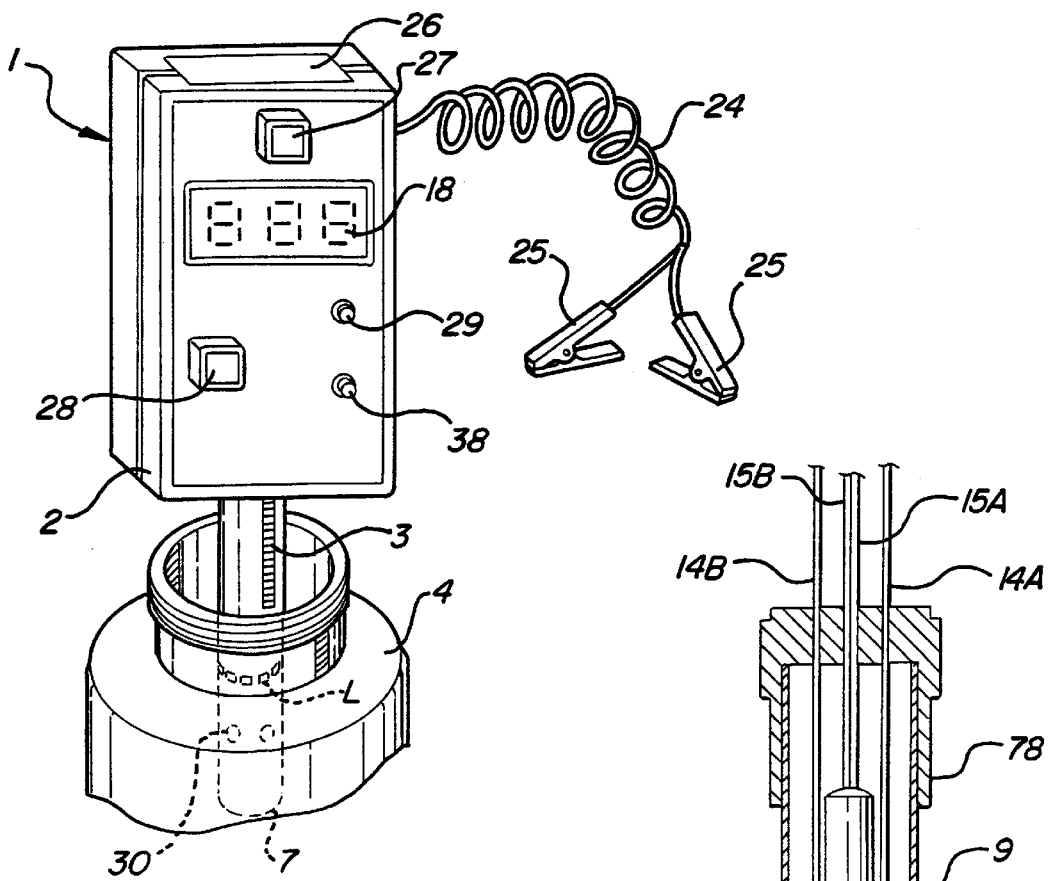
FIG. 1 shows a perspective view of a fluid boiling point meter of the present invention in use for sensing the boiling point of automotive brake fluid.
Figure 2:
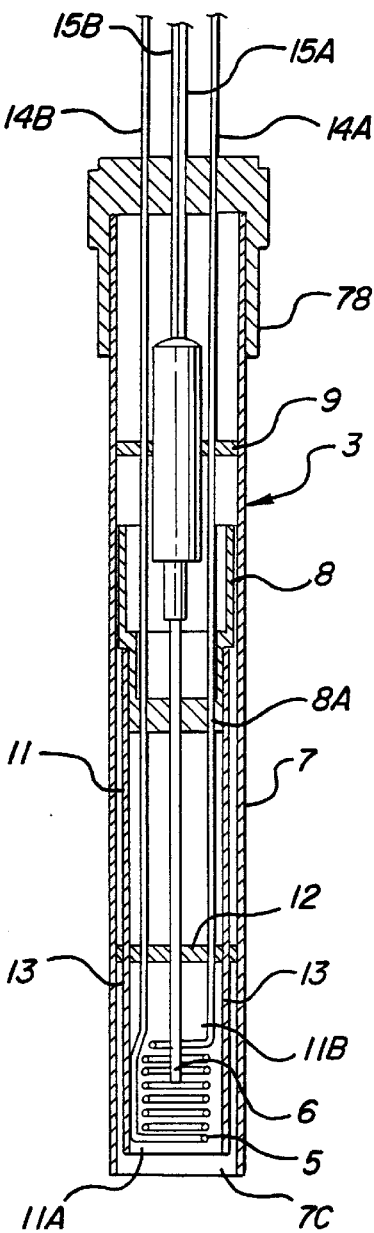
FIG. 2 shows a sectional elevation of the probe portion of the meter of FIG. 1.

Referring to FIG. 1, a temperature indicating device or meter 1 for measuring the boiling point of automotive brake fluid comprises a main casing 2 housing electronic temperature monitoring equipment and a probe 3 projecting downwardly from the casing 2 for insertion into brake fluid contained in a fluid reservoir 4 therefor as schematically illustrated and located, for example, in the engine compartment of a motor vehicle. As shown in FIG. 2, the probe 3 houses a heating element 5 for heating brake fluid while a temperature sensing head 6 of a thermocouple (serving as a mechanical electronic transducer) in the probe 3 feeds heated fluid temperature information to the temperature monitoring equipment in the casing 2.

Referring especially to FIGS. 2 and 3, the probe 3 comprises an outer tubular casing 7 while the heating element/thermocouple pack s carried by a spaced pair of heat-proof insulator members 8, 9 which in the probe assembled condition bear against the inner wall of the outer casing 7, which is provide with a cap 7B at its upper end which also serves to support the pack. A separate inner tubular casing 11 is located on a stepped portion 8A of the insulator member 8 and has an open bottom 11A which is recessed above an open bottom 7C of the outer casing 7. An annular chamber 10 is defined between the inner and outer casings 7, 11 which are advantageously made of non-corroding material such as stainless steel. A sealing ring 12 (e.g. of Tufnol (TM) is housed in the inner casing 11, and the portion of the inner casing 11 located below this ring 12 defines an inner chamber 11B wherein a portion of fluid to be tested is semi-encapsulated or entrapped, the heating element 5 and the temperature sensing head 6 being located in this inner chamber 11B. In particular, the heating element 5 is located in the lower half of the inner chamber 11B, and the temperature sensing head 6 extends into the heart of the elements. The outer casing 7 has first fluid ports 30 substantially below the sealing ring 12 and the inner casing 11 has second fluid ports 13 above the first fluid ports 30 at a level between the first fluid ports 30 and the sealing ring 12 so that when the probe 3 is inserted substantially vertically into a body of fluid to a working depth where the inner and annular chambers 11B, 10 are below the surface 31 of the fluid, fluid fills up the inner and annular chambers 11B, 10 to a level just above the first fluid ports 30. Thus upper ends 32, 33 of the inner and annular chambers 11B, 10 above the first fluid ports 30 are (initially) free of fluid with a small volume of air trapped therein. When a portion of fluid semi-encapsulated in the inner chamber 11B reaches boiling, the level of mixed fluid and vapor bubbles rises by an amount h within the inner chamber 11B until it reaches the level of the second fluid ports 13 when the boiling fluid can spill over into the annular, outer, chamber 10 at the same time drawing cooler fluid from below up into the inner chamber 11B thereby automatically preventing overheating whilst at the same maximizing the rate of initially attaining fluid boiling within the inner chamber 11B in the absence of fluid circulation.

The leads 14A/B and 15A/B for the heating element 5 and thermocouple head 6 respectively extend up through the probe 3. A suitable circuit for the electronic temperature monitoring equipment is shown in FIG. 4. The major item in this circuit is a micro-processor (up) 17 which transmits each monitored temperature value in digital form to a digital display 18 (liquid crystal form). More particularly, a temperature sensing thermocouple (T) 19 of the head 6 is connected to an amplifier and micro-powered thermocouple cold junction compensation chip (TCJC) 20, to obtain most satisfactory results. To convert the output of the matched chips into a form which the micro-processor 17 understands the output from chip 20 is fed to an analog-to-digital (A/D) converter 21 (say 10 bit). The processor 17 is driven by an erasable/programmable read-only memory (EPROM) 22 and constantly measures and monitors the temperature of the fluid within the open bottom 11A of inner tubular casing 11. The EPROM 22 holds the temperature measurement information program which is used in sensing the precise boiling point of the fluid and also to generate the BCD (binary coded decimal) code for the display 18. A suitable latch can be present between the EPROM 22 and the processor 17. The processor 17 serves to produce all the information for the various circuit items of the temperature monitoring equipment.

Once the monitoring equipment senses the fluid boiling point, the display 18 will indicate :he appropriate temperature value. Additionally, a temperature control switch (TCS) 5A for a heater 5 receives signals from the micro-processor 17 for automatically halting power to the heater 5 when the measured fluid temperature rises to a predetermined maximum level above the highest expected boiling temperature.

Power for the meter 1 can be taken from a vehicle battery via flexible leads 24 and terminal clips 25 and/or the meter 1 can carry its own battery (eg. 12 volts) for example located in housing 26. The casing 2 carries on-off buttons 27, 28 for the power supply to the heating element 5 and to the display equipment respectively, while indicator lamps 29,38 indicate when the appropriate power via button switches 27, 28 is on, although a single indicator lamp could suffice for both functions.

All the parts of the meter 1 are housed in the casing 2 or in the probe 3 and the meter 1 is a conveniently portable hand-held device.

In operation of the meter 1 to test the quality of brake fluid in a vehicle, the cap of the fluid reservoir 4 housing the brake fluid to be test ed is removed and the probe 3 is inserted into the fluid to the level indicated L. Brake fluid flows via the apertures 7C, 11A, 30 to immerse the heating element 5 and such that a semi-encapsulated body of fluid is located in the inner chamber 11B. Button 27 is now pressed to heat element 5 and consequently cause heating of the encapsulated portion of brake fluid in the open bottom 11A of inner casing 11. With button 28 actuated, the temperature monitoring equipment will monitor the increasing fluid temperature values.

The temperature rises more or less rapidly to the boiling point of the fluid. Particularly in the case of a relatively low boiling point fluid where the rate of heat loss from the inner chamber 11B would otherwise be relatively low and overheating would be likely to occur, the automatic spilling of the already boiling fluid over from the inner chamber 11B into the annular, outer, chamber 10 gives rise to a rapid increase in heat loss from the inner chamber 11B thereby helping to maintain a more or less equilibrated and steady boiling of fluid within the inner chamber 11B thereby providing a substantially stable boiling point temperature output thereby in turn facilitating the taking of accurate and reliable boiling point temperature measurements.

Figure 5:
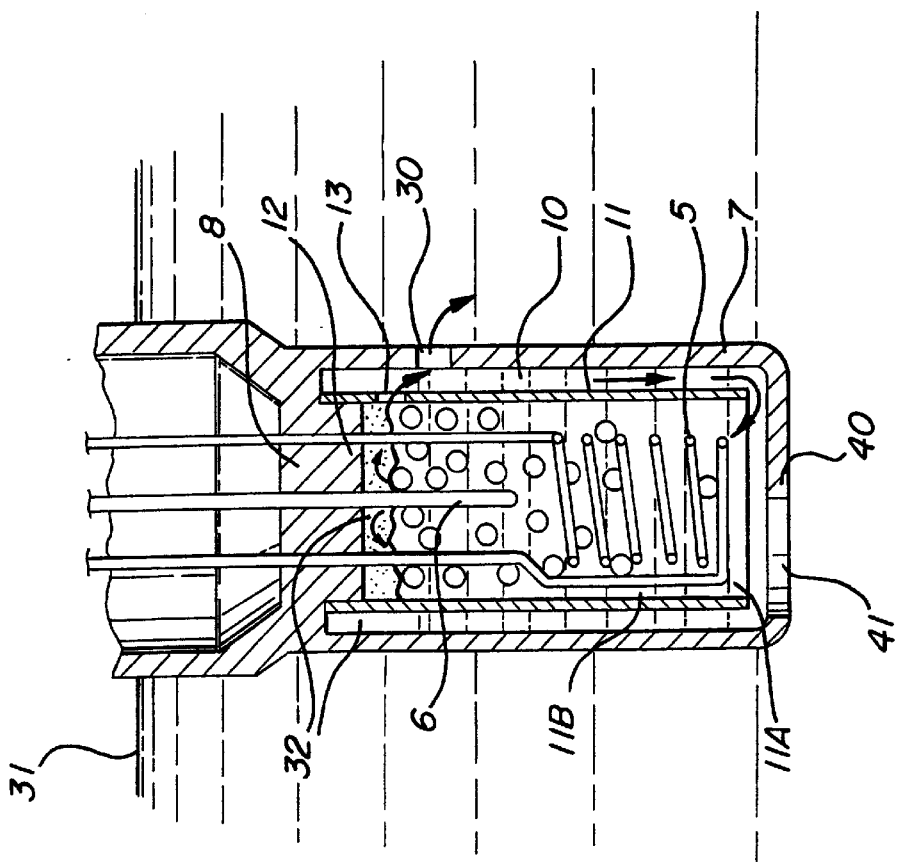

FIG. 5 is a view similar to FIG. 3 of a further embodiment in which like parts corresponding to those of the first embodiment are indicated by like reference numerals. In this case it will be seen that the base 40 of the outer casing 7 is substantially closed with a fluid inlet 41 for partially restricting flow between the inner chamber 11B and the main body of fluid.

It will be appreciated that various modifications may be made to the above described embodiments without departing from the scope of the present invention. Thus, for example, instead of a series of manually operated buttons, there could be provided a fluid level detection switch e.g. a float or capacitance switch for automatically switching on the heating element 5 and other circuitry when a portion of the probe 3 is immersed to an adequate depth (which need not however be exact) in the main body of fluid.

Figure 6:
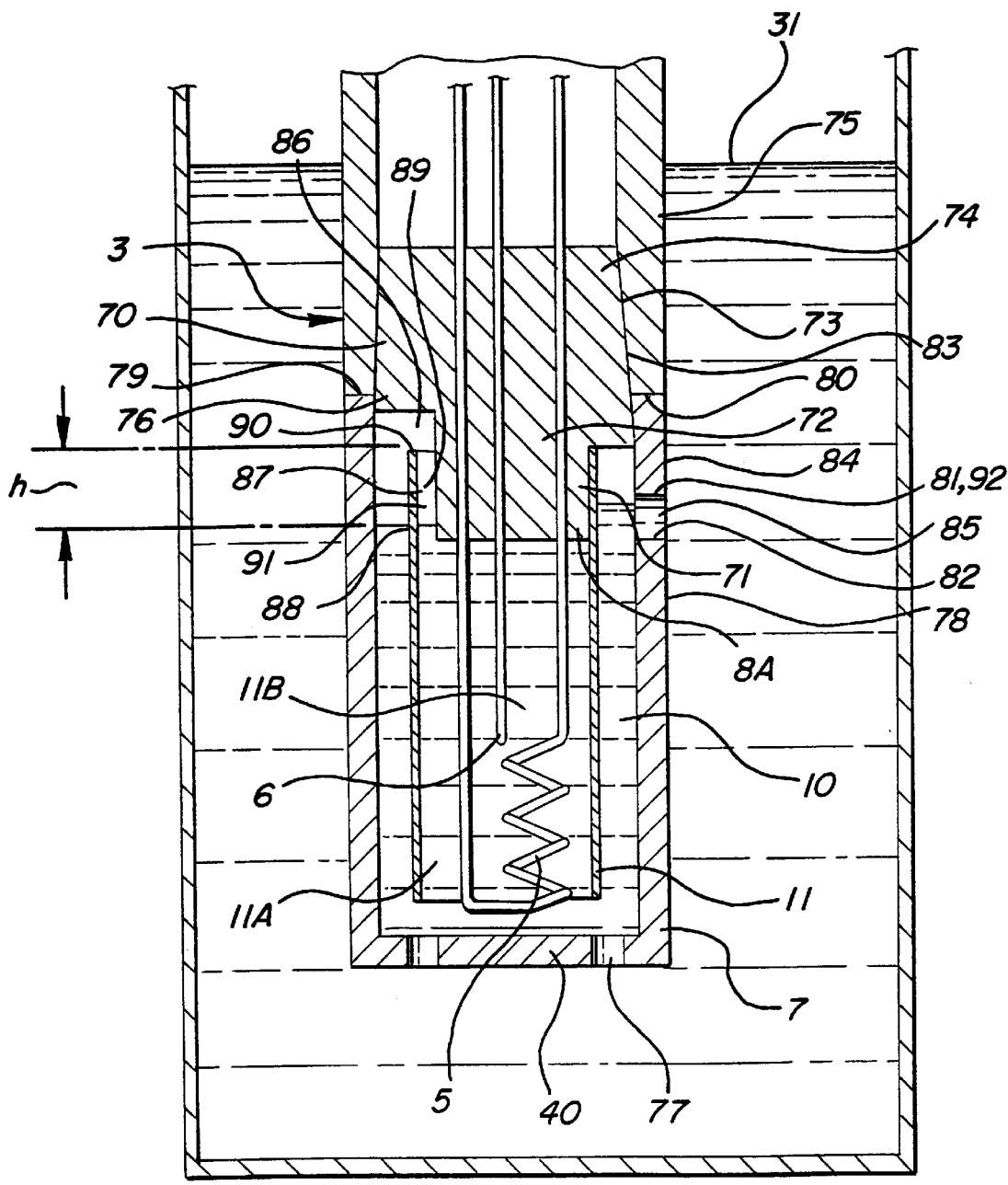

FIG. 6 shows another embodiment generally similar to that of FIG. 5 and like parts corresponding to those in FIG. 5 are indicated by like reference numerals. In this embodiment there is used a particulary convenient form of probe 3 construction with a generally cylindrical insulation member 70 having a reduced diameter portion 71 at its lower end 72 on which is push-fit mounted an inner casing in the form of a stainless steel tube 11, and a slightly tapered portion 73 at its upper end 74 on which is push-fit mounted an upper casing 75. The tubular outer casing 7 fits closely around a central portion 76 of the insulation member 70 and has a restricted fluid inlet port means in the form of a plurality of spaced apart small apertures 77 (e.g. four), in its base 40.

At one side 78, the outer casing 7 has at its upper end 79 a downwardly extending generally trapezoidal notch 80 and at whose lower end 81 is provided a further downwardly extending semi-circular notch 82. One side 83 of the central portion 10 76 of the insulation member 70 has a raised trapezoidal (in plan) portion 84, which is complementary to said trapezoidal notch 80 in the outer casing 7, the raised portion 84 thereby cooperatively defining a restricted fluid outlet port means 85 together with said semi-circular notch 82.

At its other side the central portion 76 of the insulation member 70 has a radially inwardly extending passage 86 which communicates with a longitudinally downwardly extending channel 87 formed in the adjacent outer side 88 of the lower end 72 reduced diameter portion 71. When the inner tubular casing 11 is mounted on said reduced diameter portion 71, it defines together therewith a cranked passage means 89 extending upwardly along said channel 87 from the inner chamber 11B over a "weir" constituted by the adjacent upper edge 90 of the inner tubular casing 11 along said radially extending passage 86 into the outer annular chamber 10. The difference h in the elevation levels of the radially extending passage 86 and the restricted fluid outlet port 85 at the semicircular notch 82 in the outer casing 7 means that air is trapped above the fluid and this acts as a barrier to free flow. Effectively the radially extending passage 86 linking the inner chamber 11B to the outer annular chamber 10 is maintained a few millimetres above the fluid surface 91 in the inner chamber 11B and thus fluid cannot initially flow from the inner chamber 11B to the outer chamber 10.

As discussed hereinbefore, therefore, the elevation h of the "weir" above the normal fill level 91 inside the probe 3 (which is substantially defined by the upper edge 92 of the fluid outlet port means 8 ), is restricted so as to allow fluid passage through said cranked passage means 89 upon boiling of the fluid in the inner chamber 11B whilst substantially preventing such flow during an initial heating phase before boiling temperature is reached.

Figure 7:
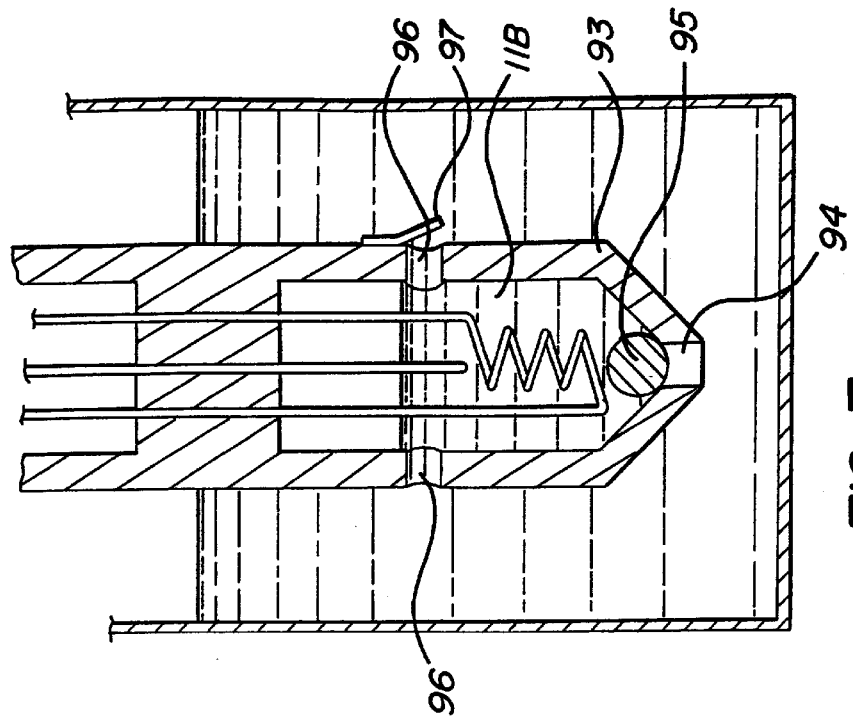
FIGS. 5 to 7 are views similar to FIG. 3 of some further embodiments.

FIG. 7 shows an alternative form of design in which there is used a single-walled body 93 having a relatively thick wall of a substantially thermally insulating material insulating the inner chamber 11B. In this case the fluid port means comprises a small restricted area inlet 94 provided with a ball valve comprising a ball 95 having a relatively low density slightly greater than that of the fluid so that the ball is only dislodged upwardly from its closed position to a partially open one by turbulent flow in the inner chamber 11B associated with boiling therein.

The fluid port means further comprises one or more restricted area fluid outlets 96 which are preferably provided with the flap valve means 97 which are displaced upwardly and outwardly from a closed position by turbulent flow associated with boiling inside the inner chamber 11B.

What is claimed is:

1. An apparatus for use in indicating the boiling point of fluids across a wide temperature range which apparatus comprises a meter of the portable hand held type including a probe portion for insertion substantially vertically into fluid in a fluid reservoir for fluid testing, heating means being provided in the probe portion for heating of said fluid, said meter including monitoring means for monitoring the temperature rise of fluid heated by said heating means for use in indicating the boiling point temperature of the fluid, said probe portion having an inner chamber, in which are located said heating means and said temperature monitoring means, said inner chamber being provided with thermal insulation means for restricting heat loss from said inner chamber, in use of the apparatus, during heating up of said fluid in the inner chamber up to its boiling point, said inner chamber being provided with port means formed and arranged so as to provide a fluid flow barrier means operable, in use of the apparatus, to allow entry of fluid into said inner chamber upon immersion of the probe portion into said fluid for semi-encapsulation of fluid in the inner chamber, and to substantially prevent loss of heated fluid therefrom to the exterior during said heating up of said fluid in the inner chamber up to its boiling point, whilst allowing a substantial loss of boiling fluid to the exterior so as to provide a substantially steady flow of fluid through said inner chamber with a controlled exchange of fluid between the inner chamber and the reservoir thereby substantially increasing heat loss from said inner chamber once said fluid has been heated to its boiling point, whereby fluid in said inner chamber may be boiled steadily without overheating.

2. Apparatus according to claim 1 wherein said inner chamber thermal insulation means comprises a thick wall means of a thermally insulating material.

3. Apparatus according to claim 2 wherein said fluid flow barrier means is in the form of valve means formed and arranged in the fluid port means for selective opening in response to the commencement of vigorous boiling in the inner chamber.

4. Apparatus according to claim 3 wherein said valve means comprises a ball valve and a flap valve each displaceable from a closed position to an open position by turbulent flow associated with the onset of boiling in the inner chamber.

5. Apparatus according to claim 1 wherein said inner chamber thermal insulation means comprises an outer wall casing means defining a generally annular outer chamber for semi-encapsulating fluid around said inner chamber.

6. Apparatus according to claim 5 wherein the fluid flow barrier means for selectively restricting fluid loss from the inner chamber comprises fluid port means in the form of a passage means extending upwardly from a fluid fill level in the inner chamber substantially defined by an opening in the outer wall casing means of the outer chamber, over a barrier at a predetermined elevation above said opening in the outer wall casing means, into the outer chamber.

7. Apparatus according to claim 6 wherein said predetermined elevation is from 1 to 5 mm.

8. Apparatus according to claim 7 wherein said predetermined elevation is from 2 to 4 mm.

9. Apparatus according to claim 8 wherein said probe portion has an insulation member mounting a generally tubular inner casing defining the inner chamber, and the outer wall casing means defining the annular outer chamber around said inner casing.

10. Apparatus according to claim 9 wherein said insulation member has channel and passage means extending between said inner chamber and said outer chamber over the barrier of said inner casing.

11. Apparatus according to claim 10 wherein said insulation member and said outer wall casing means have abutting wall portions with notch means defining a restricted fluid outlet port means therebetween.

12. A method of measuring the boiling point of a fluid comprising the steps of providing an apparatus according to claim 1; inserting the probe portion thereof into a body of said fluid; activating said heating means; and monitoring the temperature rise of fluid heated by the heating means with said monitoring means of the meter of said apparatus.

* * * * *